US012053236B2

(12) United States Patent
Bachman et al.

(10) Patent No.: US 12,053,236 B2
(45) Date of Patent: Aug. 6, 2024

(54) COOLING SYSTEM FOR SURGICAL DEVICE

(71) Applicant: Biocompatibles UK Limited, Camberley (GB)

(72) Inventors: Timothy A. Bachman, St Paul, MN (US); Charlie Senness, Hopkins, MN (US); Dennis Babcock, Maple Grove, MN (US); Jason Sprain, Shoreview, MN (US); Luan T. Chan, Coon Rapids, MN (US); Maciej W. Misiak, Eden Prairie, MN (US); Winston Tan, Plymouth, MN (US); Matthew Goulet, Bloomington, MN (US); Andrew K. Zachman, St Michael, MN (US); Logan Ernster, Minneapolis, MN (US)

(73) Assignee: Biocompatibles UK Limited, Camberley (GB)

( * ) Notice: Subject to any disclaimer, the term of this patent is extended or adjusted under 35 U.S.C. 154(b) by 295 days.

(21) Appl. No.: 16/988,168

(22) Filed: Aug. 7, 2020

(65) Prior Publication Data

US 2021/0038299 A1 Feb. 11, 2021

Related U.S. Application Data

(60) Provisional application No. 62/884,044, filed on Aug. 7, 2019.

(51) Int. Cl.
*A61B 18/14* (2006.01)
*A61B 18/00* (2006.01)

(52) U.S. Cl.
CPC ...... *A61B 18/1492* (2013.01); *A61B 2018/00035* (2013.01); *A61B 2018/00172* (2013.01); *A61B 2018/00577* (2013.01)

(58) Field of Classification Search
CPC ...... A61B 18/1492; A61B 2018/00035; A61B 2018/00172; A61B 2018/00577;
(Continued)

(56) References Cited

U.S. PATENT DOCUMENTS

| 3,662,752 A | 5/1972 | Yokoyama |
| 4,576,594 A | 3/1986 | Greenland |

(Continued)

FOREIGN PATENT DOCUMENTS

| EP | 1259204 B1 | 4/2007 |
| JP | 06-261921 A | 9/1994 |

(Continued)

OTHER PUBLICATIONS

International Search Report and Written Opinion received for PCT Patent Application No. PCT/US2020/045439, mailed on Nov. 11, 2020; 17 pages.

(Continued)

*Primary Examiner* — Linda C Dvorak
*Assistant Examiner* — Abigail Bock
(74) *Attorney, Agent, or Firm* — Pauly, DeVries Smith & Deffner LLC

(57) ABSTRACT

The disclosure provides a cooling system for a surgical ablation device, the device having a cooling circuit comprising a device coolant supply line having a supply coupling; a coolant return line having a return coupling; coolant passageways within the device to circulate coolant within the device, the supply line and the return line being in fluid communication via the device coolant passageway(s); a coolant manifold configured to fluidly connect a cooling fluid source to at least one manifold fluid outlet port, such as to place the cooling fluid source in fluid communication with (Continued)

the one or more device coolant passageways, wherein the supply coupling is configured for connection to a manifold outlet port of the manifold.

12 Claims, 9 Drawing Sheets

(58) Field of Classification Search
CPC .............. A61M 39/24; A61M 39/2039; A61M 39/268; A61F 7/00
See application file for complete search history.

(56) References Cited

U.S. PATENT DOCUMENTS

| | | | |
|---|---|---|---|
| 4,787,898 A | 11/1988 | Raines | |
| 5,454,783 A | 10/1995 | Grieshaber et al. | |
| 5,674,218 A * | 10/1997 | Rubinsky ............... | A61B 18/02 |
| | | | 606/23 |
| 6,878,156 B1 | 4/2005 | Noda | |
| 8,480,645 B1 | 7/2013 | Choudhury et al. | |
| 9,888,956 B2 | 2/2018 | Model et al. | |
| 2003/0069576 A1 | 4/2003 | Tanrisever | |
| 2005/0075705 A1* | 4/2005 | Machold ............... | A61F 7/0085 |
| | | | 607/104 |
| 2008/0027422 A1 | 1/2008 | Vancelette et al. | |
| 2008/0271796 A1* | 11/2008 | Neumann ................. | F17C 5/06 |
| | | | 137/606 |
| 2008/0308256 A1 | 12/2008 | Deborski et al. | |
| 2011/0118724 A1 | 5/2011 | Turner et al. | |
| 2013/0178709 A1 | 7/2013 | Suh et al. | |

FOREIGN PATENT DOCUMENTS

| | | | | |
|---|---|---|---|---|
| JP | 2003-524507 A | 8/2003 | | |
| JP | 2004-520864 A | 7/2004 | | |
| JP | 2013-511348 A | 4/2013 | | |
| JP | 2015-511827 A | 4/2015 | | |
| KR | 10-1728770 B1 | 4/2017 | | |
| RU | 2012125022 A * | 12/2012 | ............. | A61B 18/12 |
| WO | 2011/063061 A2 | 5/2011 | | |

OTHER PUBLICATIONS

"Final Office Action," for Japanese Patent Application No. 2022-507664 mailed Mar. 12, 2024 (7 pages) with English translation.
"Non-Final Office Action," for U.S. Appl. No. 17/144,396 mailed Jun. 5, 2024 (17 pages).

* cited by examiner

COOLING SYSTEM FOR SURGICAL DEVICE

CROSS REFERENCE TO RELATED APPLICATION

This application claims priority to Provisional Application No. 62/884,044, filed Aug. 7, 2019, which is herein incorporated by reference in its entirety.

BACKGROUND

The present invention relates to cooling systems for surgical ablation devices. Surgical ablation devices such as radiofrequency (Rf) and microwave (MW) ablation devices are well known and have been used in surgery for the ablation of tissue such as (inter alia) tumor tissue and cardiac tissue such as for the treatment of cardiac arrhythmias. Flexible catheter-type devices for navigation through passageways such as lung tissue or blood vessels as well as transcutaneous, needle type, devices are known.

During operation, portions of these devices can become hot due to the amount of energy passing through the device. Increased temperatures can lead to the device itself becoming hot and damaging surrounding tissue, but can also lead to deterioration in the properties of the antenna during use. It is common therefore for ablation devices to be cooled, typically by circulating a coolant through the device. Coolant, typically saline or water, circulating through the device has the additional advantage of modulating the dielectric properties of antennas and reducing near field anomalies that can lead to overheating of tissues close to the antenna and deterioration of impedance matching between the antenna and the tissue.

In microwave ablation, for example, antenna designers typically seek to predictably shaped field, so that the size and shape of ablations are also predictable, and so that the shape of ablation volumes may be more accurately sculpted by the use of more than one device.

One source of the coolant is IV drip-type bags, which are readily available in theatres. The coolant may be pumped through the ablation device and either discarded to waste or recirculated into the bag, to avoid the use of multiple containers. Use of multiple needles can require the use of multiple bags and hence an increase in trailing lines and time taken to set up; or use of a single bag, with multiple lines and connectors. These approaches can lead to increased complexity of set up, risks increased leaks or mistakes in set up and leads an increase in trailing lines in the theatre, which is undesirable.

The coolant may be circulated through the system by a pump and lines from the bags are connected to the pump. Again multiple devices either require multiple pumps or multiple lines attached to the same pump, which complicates set-up.

Further, it is desirable, from the point of view of cost and safety to provide systems that are easy to set up and dispose of and where minimal parts of the system are reused.

The present invention addresses at least some of these issues.

BRIEF DESCRIPTION OF THE DRAWINGS

FIG. 2A shows one arrangement of a disconnected coupling, FIG. 2B shows a connected coupling, FIG. 2C illustrates a view of a supply coupling, FIG. 2D illustrates an umbrella type valve arrangement, FIG. 2E illustrates a further view of an umbrella valve arrangement and FIG. 2F shows an enlarged view of a supply coupling and valve.

FIG. 3A illustrates a cartridge connecting a supply coupling and a return coupling to a manifold whilst bringing a pumping portion of device cooling fluid supply line into functional engagement with a peristaltic pump roller. FIG. 3B is a more detailed view of the connection of the couplings to a manifold.

FIG. 5A shows a plan view of a cooling system having a pump manifold and a cartridge comprising a demountable pump head, whilst FIG. 5B shows a sectional side view at X-Y.

DETAILED DESCRIPTION

Figure 1:
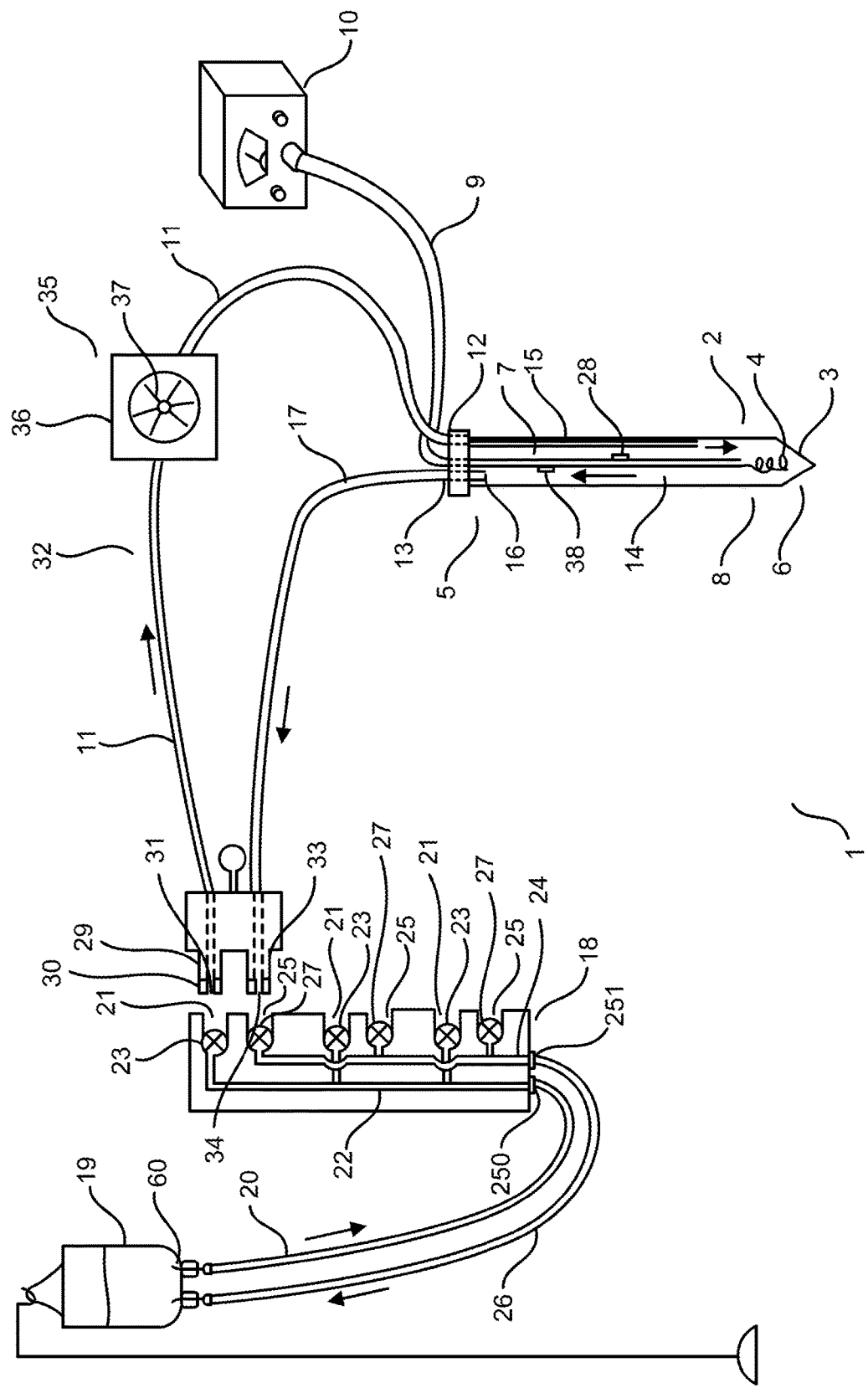
FIG. 1 is a simplified illustration of a surgical ablation system.

Thus in a first aspect, the design provides a surgical ablation system having a surgical ablation device and a coolant distribution manifold. The surgical ablation device has a device cooling circuit that includes a device coolant supply line, a device coolant return line, and one or more device coolant passageways. The device coolant supply line may be configured to deliver coolant to the ablation device, and the device coolant supply line includes a supply coupling. The device coolant return line may be configured to receive coolant outflow from the ablation device. The one or more device coolant passageways within the ablation device may be configured to circulate coolant within the device for cooling at least a portion of the device. The device coolant supply line and the device coolant return line may be in fluid communication via the device coolant passageway(s). The coolant distribution manifold may be configured to fluidly connect a cooling fluid source to at least one manifold fluid outlet port. The supply coupling may be configured for connection to the manifold outlet port such as to place the cooling fluid source in fluid communication with the one or more device coolant passageways.

The manifold may be further configured to fluidly connect the cooling fluid source to the manifold outlet port, via a normally closed manifold outlet valve, the supply coupling may be configured to cause the manifold outlet valve to open upon connection to the manifold outlet port, such as to place the cooling fluid supply in fluid communication with the one or more device coolant passageways.

The manifold may be additionally comprise one or more manifold inlet ports and may be configured to fluidly connect a cooling system return to the one or more manifold inlet ports. The device coolant return may comprise a return coupling configured for connection to the manifold inlet port such that the cooling system return may be placed in fluid communication with the one or more device coolant passageways.

The manifold may be further configured to fluidly connect the cooling system return to the manifold inlet port via a normally closed manifold inlet valve. The manifold inlet valve may be opened or closed to allow connection of the return coupling to the port. The return coupling maybe further configured to cause the manifold inlet valve to open upon connection to the manifold outlet port, such as to place the cooling fluid return in fluid communication with the one or more device coolant passageways.

The ablation device is configured to deliver ablation energy to a patient tissue to ablate the tissue. The ablation device may be any type of ablation device where cooling of at least one part of the device is desirable, this includes, for example microwave ablation devices and Rf ablation devices, both of which are well known in the art. The device may be a transcutaneous ablation probe, such as a needle. Such needles typically have a tip configured to penetrate tissue and a relatively rigid shaft, such that the device tip can be advanced through tissue. Alternatively the device can be an ablation catheter, typically having a flexible shaft configured for passage through body passageways such as lung passageways, gut passageways, urinary passageways, and passageways of the reproduction system or blood vessels. Such devices may be configured for penetration of tissues or may be blunt ended.

Ablation devices typically comprise an elongate shaft having a proximal end and a distal end. The shaft terminates distally in a tip, which may be configured for penetration of tissue or may be blunt, to reduce tissue trauma. The shaft may enclose an ablation energy supply line, which may be, for example, a coaxial cable having an inner conductor an outer conductor and a dielectric there between. The device comprises, distally, a radiating region configured to deliver ablation energy to the tissue. The device may have one of a variety of antenna configurations, depending on the ablation modality. The proximal end of the feedline may be attached to a cable (typically a coaxial cable) connecting the device to an energy generator for providing ablation energy to the device.

The ablation device is provided with one or more internal coolant passageways configured to circulate coolant within the device. These passageways allow the coolant to cool the device or parts thereof, and are typically in fluid communication with a device coolant supply line configured to deliver coolant to the internal coolant passageway(s) of the device and a device coolant return line carrying coolant away from the passageway(s). Thus the device coolant supply line and the device coolant return line may be in fluid communication with each other via the internal coolant passageways of the device.

The internal coolant passageway or passageways are arranged to cool features of the device, for example the passageways may be arranged to cool, inter alia, at least a part of any of the following, if present: the feedline, the sheath, an antenna, a radiating portion, a choke, a balun, a device tip, a hub, or any other portion or feature of the device as required.

The device has a device coolant inlet and a device coolant outlet to which the device coolant supply line and coolant return lines may be respectively, permanently connected, or the lines may be provided with releasable couplings such as LuerLok® fittings for releasable connection. Optionally they are permanently connected to reduce the number of connections to be made in set up.

The system additionally comprises a manifold configured to distribute cooling fluid from a source of coolant fluid, such as an IV bag, to one or more surgical ablation devices and may also receive returning coolant from the devices and pass the returning fluid either back to the source, or to waste.

The use of a coolant distribution manifold allows one, or more than one, particularly at least two (such as two, three or more), devices to be fluidly connected to the same source of coolant according to the needs of the procedure, using only one pair of coolant supply lines: a coolant system supply line fluidly connectable between the manifold and the coolant fluid source and a coolant system return line connectable between the manifold and the coolant fluid source or to waste. In this way the number of lines between a cooling fluid source to the pump, can be reduced, reducing the possibility for leaks and errors in connecting up the lines. In order to keep the number of fluid filled containers to a minimum, the cooling fluid return line may be configured to return the cooling fluid to the cooling fluid source to form a recirculating cooling system. Thus the coolant fluid supply line and the coolant fluid return line may comprise connectors for reversible connection to a source of coolant or waste as appropriate.

The manifold is configured to fluidly connect a cooling fluid source to at least one manifold fluid outlet port, particularly via a normally closed manifold outlet valve. Optionally the manifold is also configured to fluidly connect a coolant system return line to a manifold fluid inlet port, particularly via a normally closed manifold fluid inlet valve. The cooling fluid source may be fluidly connected to the manifold via a coolant system supply line, whilst coolant system return line fluidly connects the manifold to waste, or to the cooling fluid source, to recycle the cooling fluid. The coolant system supply line and the coolant system return line are optionally permanently connected to the manifold to provide a convenient, connector free, system.

The manifold optionally comprises a manifold supply conduit in fluid communication with the coolant system supply line. The manifold inflow conduit is configured to distribute the coolant from the coolant supply to the manifold outlet ports. Typically the conduit is branched, having one branch in fluid communication with each manifold outlet port. The manifold supply conduit is fluidly connected to one or more such outlet ports, and in one advantageous embodiment it may be fluidly connected via a normally closed, manifold outlet valve.

In this approach, each branch of the manifold supply conduit comprises one manifold outlet valve in fluid communication with a manifold outlet port. These valves prevent cooling fluid from flowing out of the outlet port, unless the outlet valve is opened. The valve may be a one way valve or check-valve, such as a check valve that normally operates on a pressure differential between the inlet side and the outlet side. Valves such as those of a type known as an umbrella valves or a duckbill valves may be employed.

Connection of the supply coupling to the manifold outlet port opens the manifold outlet valve and places the manifold supply conduit in fluid communication with the device coolant supply line, and therefore places the cooling fluid supply, directly or indirectly, in fluid communication with the device coolant passageways.

The manifold outlet valve may be opened in a number of ways by connection of the supply coupling. In one example an actuator within the port, may be contacted by the supply coupling and may be displaced. Displacement of the actuator may cause opening of the valve. Alternatively the valve may be configured such that the distal end of the coupling contacts the valve and displaces it from its seat during coupling, for example a ball valve may be displaced from its seat in this manner, or the disc of an umbrella valve may be lifted. In one arrangement the seat of an umbrella valve may comprise passageways that receive projections arranged at the distal end of a supply coupling. In this way the projections may pass through the valve seat and displace the valve from its seat. In the case of a duckbilled valve, for example connection of the coupling may cause the distal portion of the coupling to contact the duckbill portion causing it to open, e.g., an extension of the coupling may displace the sides of the "bill" allowing fluid to flow.

The manifold may also comprise a manifold return conduit in fluid communication with the coolant system return line. The manifold return conduit is configured to collect the coolant from each manifold inlet port. Typically the inlet conduit is branched, having one branch in fluid communication with each manifold inlet port. In an advantageous embodiment, the return conduit is fluidly connected to one or more such inlet ports, each via a separate, normally closed, manifold inlet valve. Thus each branch of the manifold return conduit may comprise one manifold inlet valve in fluid communication with a manifold inlet port. These valves are configured to prevent cooling fluid from flowing out of the inlet port, (that is to say, in a direction that would be against the return flow), unless the outlet valve is opened. In one advantageous embodiment, the manifold inlet valves may be configured to be opened by return flow from the device, although they may alternatively be configured to be opened upon connection of the return coupling in the same way as the manifold outlet valve. In either case, the valve may be a one way valve or check-valve. It may be a check valve that operates on a pressure differential between the inlet side and the outlet side, opening in response to higher pressure on the inlet side. In particular, the manifold inlet valve may also be of a type known as an umbrella valve. In an optional embodiment, therefore, connection of the return coupling to the manifold inlet port places the manifold supply conduit in fluid communication with the device coolant return line, and therefore places the device coolant passageways, directly or indirectly, in fluid communication with the cooling fluid return line only when fluid pressure is higher on the device side of the valve, than the manifold side, for example when fluid is pumped around the circuit.

The ports may be arranged in inlet-outlet pairs, to make connection easier. The flow through each pair of manifold inlet ports and manifold outlet ports may be arranged in parallel with that through the other port pairs. With this arrangement, flow disturbances such as blockages in the coolant circuit of one device do not affect the flow through any others on the same manifold and further, devices can be connected and disconnected from any pair of ports without interrupting flow in the others. The provision of manifold outlet valves and manifold inlet valves each configured to prevent outflow from the manifold, reduces the chance of leakage from the manifold during set-up and/or if one or more pairs of ports are not used.

The manifold inlet ports and manifold outlet ports may be either of the male format, or the female format, according to the design of the supply and return coupling. Each port has a proximal end orientated towards the manifold and a distal end orientated away from the manifold. In one advantageous embodiment, the manifold outlet port comprises a manifold outlet valve since this arrangement makes it easier for connection of the supply coupling to the port to open the valve. The manifold inlet port may be also arranged in this manner.

The ports are optionally of a female configuration with the valve arranged towards the proximal end of the port (i.e. towards the base end). The ports optionally have port walls of a generally frustoconical shape, tapering towards the base for ease of connection, and may comprise a seal, such as an O-ring seal configured to engage with the supply or return coupling respectively to prevent leakage. Alternatively the O-ring may be arranged on the coupling.

The device coolant circuit is provided with a coolant inlet through which coolant may enter the circuit, from the manifold, and a coolant outlet through which coolant may leave the circuit to return to the manifold. The device cooling circuit is configured to be connectable to the manifold such as to place the cooling fluid supply in fluid communication with the one or more device coolant passageways and optionally such as to also place the device coolant passageways in fluid communication with the coolant supply to recycle the coolant or to waste.

The device coolant supply line comprises a supply line coolant inlet. Optionally the supply line comprises a supply coupling, which is disposed at the coolant inlet configured for connection to a manifold outlet port, and which is described in more detail below. In one advantageous embodiment, the supply coupling is configured to cause a manifold outlet valve to open upon its connection to the manifold outlet port.

The supply coupling has a proximal end oriented towards the device coolant supply line and a distal end oriented away from the supply line; and may comprise a supply coupling coolant conduit, which comprises the coolant inlet, and which is in fluid communication with the device coolant supply line. This enables the coupling to place the manifold coolant inflow conduit, and hence the coolant supply, in fluid communication with the device coolant supply line when the device is connected to the manifold as described herein. The supply coupling may be of a male or female format, but may be of the male format. The coupling may be configured to make a fluid tight connection to the manifold outlet port, such that fluid from the manifold may be delivered to the device coolant supply line for cooling the device, without leaks. In one advantageous arrangement the supply coupling is of the male format, and optionally of a generally frustoconical shape, tapering towards the distal end.

In one advantageous embodiment, connecting the supply coupling with the manifold outlet port causes the manifold outlet valve to open. The supply coupling may be for example, configured to contact the manifold outlet valve upon connection and thereby cause it to open. The coupling may, for example, comprise one or more features that are configured to cause the manifold outlet valve to open upon connection of the coupling to the port. These feature(s) may comprise, for example one or more projections configured to contact the valve and open it upon connection.

Projections may for example, press a ball of a ball valve off its seat or may lift the disc of an umbrella valve or part the sides of a duckbill valve. This arrangement is particularly useful where the coupling is of the male format, where the features are optionally provided towards the distal end of the coupling, although projections may also be used where the coupling is of the female format.

The device coolant return line may be configured to return the coolant fluid to waste or to return the fluid to the fluid supply. In this way the returned fluid may be recycled. The device coolant return line comprises a return line coolant outlet. In an advantageous arrangement, the device coolant return line comprises a return coupling. The return coupling is disposed at the coolant outlet and configured for connection to a manifold inlet port, and which is described in more detail below. The coupling comprises a return coupling coolant conduit, which comprises the coolant outlet, in fluid communication with the device coolant return line. This enables the coupling to place the manifold outflow conduit in fluid communication with the device coolant return line when the device is connected to the manifold. The coupling may be of a male or female format, but may be of the male format. The return coupling may cause the manifold inlet valve to open upon connection, such as in the same manner as described for the supply coupling. In one approach the manifold inlet valve is configured to be opened by return flow from the device.

In one advantageous embodiment supply and return couplings are disposed in an arrangement configured for simultaneous connection to the manifold fluid outlet port and manifold fluid inlet port respectively. This provides a more stable coupling to the manifold and improves the ease with which the ports are connected. The supply and return couplings may, for example be mounted together, on cartridge or cartridge, such as a plug, which holds them in a configuration for simultaneous insertion into the supply and return ports.

In a further advantageous embodiment the ablation system may additionally comprise a pump configured to pump cooling fluid through the cooling circuit and thus through the coolant passageways of the device. The pump may comprise a pump head, which comprises a pumping mechanism, for example, it may comprise at least one peristaltic roller, pump vane, pump gear, pump impeller, pump rotor, pump screw, pump piston or pump diaphragm; and the fluid conduits upon which, or within which, the pumping mechanism acts in order to pump the fluid. The pump head may be configured for demountable connection to a pump head drive. The pump may additionally comprise a pump head drive configured to drive the pump head (including the fluid driving mechanism) to pump the cooling fluid through the cooling circuit. Demountable pump heads may also comprise a drive coupling configured to engage a pump head drive. The pump may comprise a pump motor configured to drive the pump drive. The pump may be disposed in the cooling circuit between the cooling circuit inlet and the cooling circuit outlet.

In one embodiment the cooling circuit is configured to be connected to the pump such that the cooling fluid can be pumped around the cooling circuit, alternatively the cooling circuit comprises a pumping portion configured for demountable connection to a pump drive, connection to the pump drive then enables the cooling fluid to be pumped around the circuit. Either the device coolant supply or the device coolant return may comprise the pumping portion. The fluid conduits may be in fluid communication with the device coolant passageways.

In one advantageous embodiment, the pumping portion comprises a demountable pump-head configured for reversible attachment to a pump drive. The pump head may then be disposable. The pump head may be permanently fluidly connected to the device cooling circuit. The pump head may comprise a pumping mechanism, which may be at least one peristaltic roller, pump vane, pump gear, pump rotor, pump screw, pump piston, pump impeller or pump diaphragm; and the fluid conduits upon which, or within which, the pumping mechanism acts in order to pump the fluid. The pump head may be configured for demountable connection to a pump drive, configured to drive the fluid driving mechanism to pump the cooling fluid through the cooling circuit.

In one advantageous embodiment, the cooling circuit may comprise a pump tube configured for releasable engagement with a pump head of a peristaltic pump. The pumping portion may be a region of the device cooling circuit configured as the pump tube. The pump tube is in fluid communication with the device coolant passage ways. The tube will be, either directly or indirectly, in fluid communication with the device coolant supply line and so the action of the pump rollers on the tube will pump the coolant through the device coolant passageways. The pumping portion (the pump tubing) may be separate from the pump and lacks the pump head and rollers, thus the cooling circuit and device need not be supplied along with the mechanical portions of the peristaltic pump.

The tube may conveniently be a portion of the coolant supply or return line, of suitably resilient material (e.g. polymer based tubing such as silicone, thermoplastic elastomer, such as Bioprene, PVC) or may be a suitable length of resilient tubing forming at least a part of the supply or return line. The device coolant supply line or the device coolant return line may comprise the pump tubing. The pump tubing may be configured for releasable functional engagement with the peristaltic pump head (i.e. with the rollers).

The pump tube may comprise fastenings to hold the tubing in such engagement with the pump head.

In one advantageous embodiment, the pump tubing may be held in a cartridge configured to hold the pump tube in releasable engagement with the pump head rollers.

In one advantageous embodiment, the supply coupling and optionally the return coupling may be disposed as components of a cartridge, which may additionally comprise the pumping portion, such as the pump head particularly the fluid driving mechanism drive coupling (or the tube of a peristaltic pump). This approach is useful because it facilitates their manipulation as a single piece. This has the advantage for example, that it allows multiple connections to be made with one manipulation. The supply and return couplings may be disposed in an arrangement configured for simultaneous connection to the manifold fluid outlet port and manifold fluid inlet port respectively. The cartridge allows the pump head and particularly the fluid driving mechanism drive coupling (or the tube of a peristaltic pump) to be held in a fixed spatial arrangement with the supply and return couplings so that the three components are configured for connection of the couplings to the ports at the same time as the pump head, and particularly the fluid driving mechanism drive coupling (or the tube of a peristaltic pump) are connected to the pump drive.

Where the pumping portion comprises a demountable pump head, the cartridge may be additionally configured to bring the pump head into releasable engagement with a pump head drive. The cartridge may be configured such that the supply coupling and the return coupling may be simultaneously connected to a manifold inlet port and outlet port respectively, as the pump-head is brought into engagement with the pump drive.

The cartridge may be further configured to guide the supply coupling and return coupling into connection with the inlet and out let port, to guide the pump-head into engagement with the pump drive or both. The cartridge may comprise for example features configured for mutual guiding engagement with the manifold, the pump or both. These features include for example guide pins that engage with guides, such as slots or holes on the manifold or vice versa or slides engaging with runners. Alternatively or additionally, the pump head may be received in a depression in the pump housing configured to receive the pump head, or vice versa. For example, either or both may be configured to be received in one orientation only.

The cartridge may also be configured for clamped engagement with the pump, such as to hold the pump head in engagement with the pump head drive.

Where the pumping portion comprises the pump tube of a peristaltic pump, the pump tube may be disposed in a cartridge configured for releasable engagement with a peristaltic pump, such as to hold the pump tube in releasable engagement with the pump head rollers.

The cartridge may conveniently additionally comprise a surface configured to receive the pump tube; the surface may be a surface against which the resilient tube is arranged to be compressed by the rollers during operation of the pump, for example. The surface may have the shape of a segment of a circle, and may additionally comprise a groove extending at least along a portion of the surface for receiving the pump tube.

The cartridge may additionally comprise the supply coupling arranged for connection to a manifold outlet port; optionally the cartridge comprises both the supply and return couplings, which may be disposed in an arrangement configured for simultaneous connection to the manifold fluid outlet port and manifold fluid inlet port respectively.

In order to improve the accuracy of location of the couplings, the cartridge and the manifold may be configured for guiding engagement (other than between the ports and the couplings) to guide the supply and return couplings into connection with the respective manifold ports. For example, the manifold may be configured to receive a portion of the cartridge in sliding and/or guiding engagement. The cartridge may also be configured for clamped engagement with the peristaltic pump, such as to hold the pump tube in functional engagement with the rollers.

The cartridge may additionally comprise support for the device coolant supply and/or return lines, such as clips or other features configured to hold the lines in place.

In order to assist in guiding the pump tube into engagement with the pump rollers, the cartridge may be configured for guiding engagement with the pump. For example, the pump housing or other portions of the pump may be configured for guiding engagement with the cartridge, or vice versa.

In order to assist setup, the manifold may be configured for releasable engagement with the pump (for example with the pump housing). This holds the manifold in place whist the system is set up. For example the manifold may comprise one or more releasable couplings configured to engage with a portion of the pump, such as the pump housing or vice versa. Alternatively, or additionally, the manifold may be configured to engage with a recess in a portion of the pump, such as the pump housing.

It is also advantageous that the system is configured to hold the manifold ports in a fixed spatial arrangement with the pump. When the pump head is demountable the manifold ports may be held in a fixed spatial arrangement with a pump drive, spindle or drive coupling, for example. When the pumping portion is a pump tube, then the manifold ports may be held in a fixed spatial arrangement with the pump head rollers, for example. This helps the couplings to be guided into connection with the ports at the same time as the pump tube is guided into engagement with the pump drive or pump rollers. This approach is particularly useful where the pump head or pump tube and couplings are disposed as components of a cartridge, as it facilitates their manipulation as a single piece.

Thus, in one approach, the manifold and pump are configured for releasable engagement such as to hold the manifold ports in a configuration with the pump (for example with the pump drive or with the pump head rollers) such as to allow connection of the couplings to the ports and to allow the pump tube to be brought into engagement with the pump head rollers (or to allow the pump head to be brought into engagement with the pump drive).

For example, the manifold may be configured for releasable engagement with the pump (for example the pump housing), in an arrangement configured to hold the outlet and inlet ports in a fixed spatial arrangement with the drive or the pump rollers as appropriate. The manifold may comprise one or more releasable couplings configured to engage with a portion of the pump, such as the pump housing or vice versa. Alternatively, or additionally, the manifold may be configured to engage with a recess in a portion of the pump, such as the pump housing In a second aspect, the design additionally provides a surgical ablation device as described herein for use in the ablation system of the first aspect. The invention therefore also provides a surgical ablation device comprising one or more device coolant passageways internally, for passing coolant fluid to cool at least a portion of the device; the ablation device provided with: a device coolant supply line configured to deliver coolant to the device coolant passageways, the device coolant supply line comprising a supply coupling; a device coolant return line configured to receive coolant outflow from the device coolant passageways, the device coolant supply line and the device coolant return line being in fluid communication via the device coolant passageway(s); the device coolant supply line the coolant passageways and the device coolant return line defining a cooling circuit segment between the supply coupling and the return coupling; the cooling circuit segment comprising a pumping portion configured for pumping cooling fluid through the device coolant passageways.

The device coolant return line may comprise a return coupling. The supply coupling may comprise one or more projections.

The supply, and return couplings where present, may be disposed, on a cartridge which additionally comprises the pumping portion as described elsewhere herein. The pumping portion for example, may comprise a demountable pump-head configured for releasable engagement with a pump drive or may comprise a tube configured for use as the pump tube of a peristaltic pump, which may be configured for releasable engagement with the pump head of a peristaltic pump. The tube may, for example be disposed on a cartridge as described elsewhere herein, which cartridge may additionally comprise the supply coupling and optionally the return coupling. The supply coupling may be configured for connection to a manifold outlet port of a coolant distribution manifold and the return coupling is configured for connection to a manifold inlet port of the coolant distribution manifold. Particularly, the coolant distribution manifold may be configured to fluidly connect a cooling fluid supply to at least one manifold fluid outlet port and to connect at least one coolant return to a cooling system return.

In a third aspect, the design additionally provides a coolant distribution manifold for distributing coolant fluid to one or more surgical ablation tools as described herein, in the first and second aspects. The design therefore also provides a coolant distribution manifold for distributing coolant fluid to one or more surgical ablation devices. The coolant distribution manifold may include a manifold fluid supply inlet, a manifold fluid return outlet, at least one manifold fluid outlet port, at least one manifold fluid inlet port, and a manifold inflow conduit, and a manifold outflow conduit. The manifold inflow conduit may be configured to distribute cooling fluid from the manifold fluid supply inlet to each manifold fluid outlet ports. The manifold outflow conduit may be configured to distribute cooling fluid from each manifold fluid inlet port to the manifold fluid return outlet. The supply conduit may be in fluid communication with each outlet port via a normally closed manifold outlet valve. Each manifold outlet port may be configured for fluid tight connection to a supply coupling. Each manifold outlet valve may be configured to be opened by connection of a supply coupling to the outlet port.

In an advantageous embodiment, the return conduit may be in fluid communication with each inlet port via a normally closed manifold inlet valve. Each manifold inlet port may be configured for fluid tight connection to a supply coupling. Each manifold inlet valve may be configured to open upon connection of the supply coupling to the outlet port.

The manifold fluid supply inlet may be configured for connection to a system fluid supply line, such as for example by the provision of a connector, such as a LuerLoK® type connector or the fluid supply inlet may be permanently connected to a system fluid supply line. Likewise, the manifold fluid return inlet may be similarly configured or the fluid return inlet may be permanently connected to a system return line.

The design will now be described further by way of the following non limiting examples with reference to the figures. These are provided for the purpose of illustration only and other examples falling within the scope of the claims will occur to those skilled in the art in the light of these. All references cited herein are incorporated by reference in their entirety. Any conflict between that reference and this application shall be governed by this application.

FIG. 1 is a simplified illustration of a cooling system according to the invention. The system 1 comprises an ablation device, in this case a microwave ablation probe in the form of a microwave ablation needle 2 which is configured to deliver microwave energy to a patient tissue to ablate the tissue. The cooling system may also be used in relation to other cooled ablation devices such as radiofrequency (Rf) ablation devices for example.

The microwave ablation device 2 has a tip 3 configured to penetrate tissue and an elongate shaft having a proximal end 5 and a distal end 6. The shaft encloses a coolant passageway 14 and a feedline, 7 which may be a coaxial cable having an inner conductor an outer conductor and a dielectric there between (not shown in this figure). The feedline comprises, distally, a radiating region 8 comprising a microwave antenna 4. The proximal end of the feedline 7 may be attached to a cable 9 (typically a coaxial cable) connecting the device 2 to a microwave generator 10 for providing microwave energy to the device. The cable may be releasably connectable, or, as in this case, permanently attached to the device.

The device is provided with coolant via a device coolant supply line 11 which may be permanently attached to the device coolant inlet 12. In some embodiments, the device coolant supply line may, alternatively, be releasably connectable to the coolant inlet 12 such as via a Luer® type connector. The device coolant inlet 12 is in fluid communication with the device coolant outlet 13, via a series of coolant passageways 14, 15, 16 configured to circulate coolant within the device. In this simplified representation, coolant enters the device through the coolant passageway 15 via the coolant inlet 12, circulates through a coolant passageway 14 to cool the device, and leaves via the coolant outlet tube 13 and device coolant return line 17.

The system 1 is provided with a manifold 18 which receives coolant fluid from a coolant fluid source 19, via a coolant system supply line 20. The coolant system supply line 20 may be permanently connected to the manifold 18 at the manifold fluid supply inlet 250 or it may be releasably connectable to the supply inlet 250, for example by a LuerLok® connector. The coolant fluid source may be, for example, an IV bag. The in-flowing coolant may be distributed to one or more manifold outlet ports 21, via a manifold inflow conduit 22. In an advantageous embodiment, and as illustrated in FIG. 1, flow of coolant out of the port 21 may controlled by a manifold outlet valve 23. This valve may be normally in the closed position.

The manifold 18 also comprises a manifold coolant outflow conduit 24 which provides a fluid connection between one or more manifold fluid inlet ports 25 and the coolant system return line 26. The coolant system return line 26 may be permanently connected to the manifold 18 at the manifold fluid return inlet 251 or it may be releasably connectable to the supply inlet 250, for example by a LuerLok® connector. In an advantageous embodiment, a manifold inlet valve 27 controls the flow through each inlet port and may also normally be in the closed state.

A supply coupling 29 is configured for connection to a manifold outlet port 21. The system may also comprise a return coupling 33 which configured for connection to a manifold inlet port. In an advantageous embodiment, the manifold outlet valve 23 may be configured to open upon connection of the supply coupling 29. In one approach, the supply coupling may comprise projections 30 which cause the valve to open upon connection of the coupling 29, to the port 21, but other arrangements are possible as discussed elsewhere herein.

A coolant circuit coolant inlet 31 on the supply coupling 29 is in fluid communication with the device coolant supply line 11 so that connection of the supply coupling 29 to the outlet port 21 places the cooling circuit 32 in fluid communication with the cooling fluid supply 19.

A return coupling 33 may have a coolant circuit outlet 34 in fluid communication with the device coolant return line 17. The supply coupling 29 and the return coupling 33 can be arranged for simultaneous connection to the manifold outlet port 21 and inlet port 25 respectively.

A pumping portion 35 may be arranged in the device cooling circuit 32 and may be arranged in the supply line 11 for example, and is arranged to circulate the coolant through the device 2. In this instance the pump is a disposable pump head 36 having pump vanes 37, permanently connected in the device coolant supply line and adapted to be connected to a pump head drive (not shown). Alternative pumping portions are described elsewhere herein.

Figure 2A:
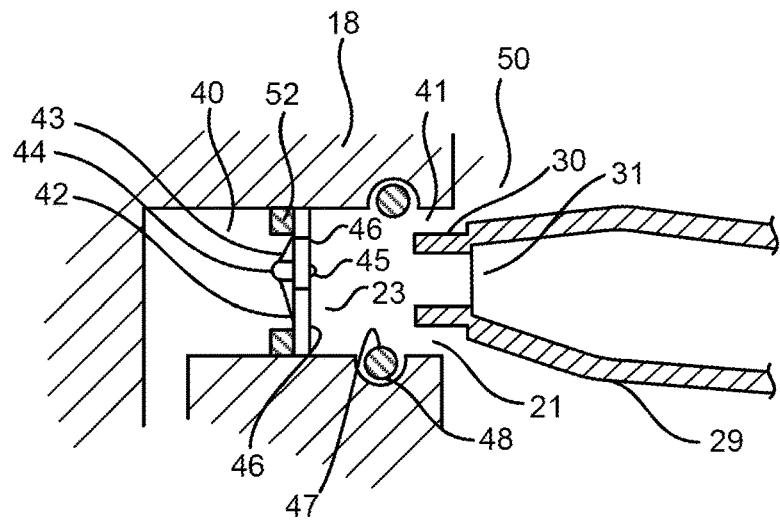
FIGS. 2A-F illustrate one arrangement of a manifold outlet port and a supply coupling.
Figure 2B:
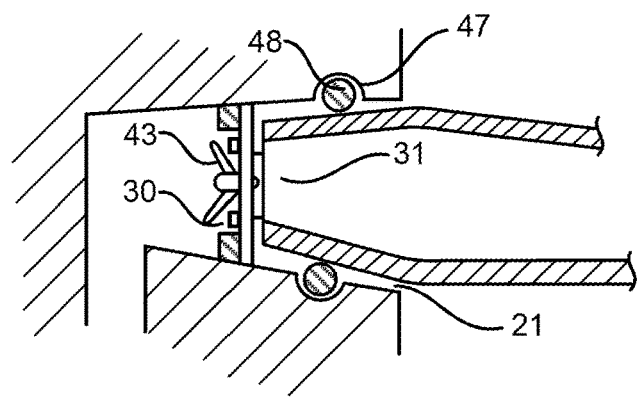
Figure 2C:
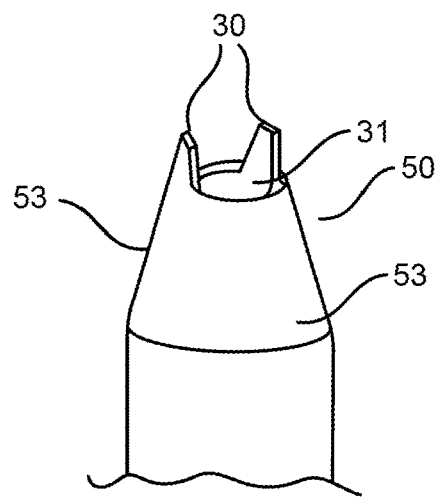
Figure 2D:
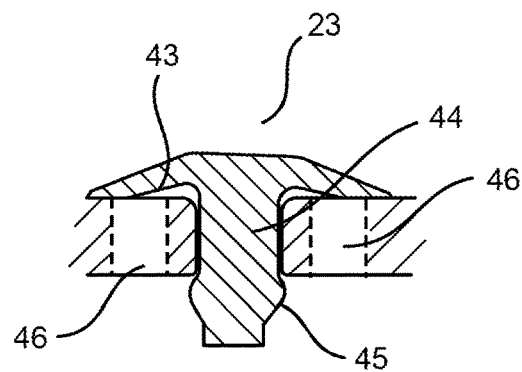
Figure 2E:
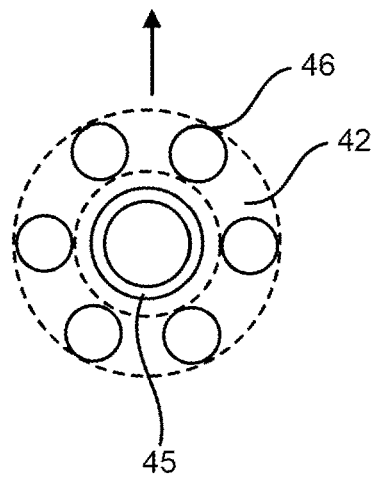
Figure 2F:
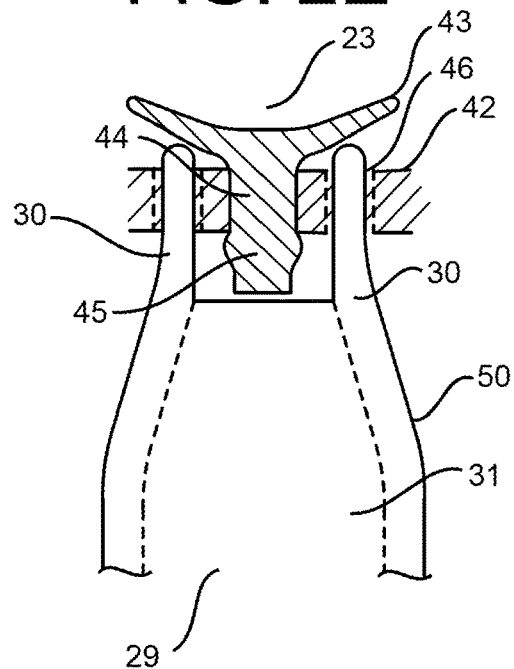

FIGS. 2A-F illustrate one arrangement of the manifold outlet port and supply coupling. FIG. 2A illustrates a disconnected coupling and FIG. 2B illustrates a connected coupling. FIG. 2C is a view of a portion of a supply coupling. FIG. 2D is a detailed cross section of an umbrella valve and its sea. FIG. 2E is an illustration of a valve and seat viewed from below. FIG. 2F is an enlarged view of a connected supply coupling.

A manifold 18 comprises one or more manifold outlet ports 21 having a proximal end 40 and a distal end 41. In an advantageous embodiment, an outlet port may comprise a manifold outlet valve 23. The valve may be disposed towards the proximal end 40 of the port, and may be held in place against an annular ridge 52. In one approach, the outlet valve 23 may be an umbrella valve having a valve seat 42 and a valve diaphragm 43 supported on a stem 44 passing through the seat 42 and held in place by a retainer 45. The umbrella valve diaphragm 43 may comprise an elastomeric material and may be unitary with the stem 44 and retainer 45. The diaphragm 43 closes one or more flow passageways 46 and prevents outflow from the port 21. This arrangement is shown in more detail in FIGS. 2D and 2E. The port may comprise an "O" ring seal 47 which may be held within a retaining groove 48 and seals against the supply coupling 29.

In one approach, the supply coupling 29 comprises one or more projections 30 at its distal end 50 which pass through flow passageways 46 and displace the valve diaphragm 43 from its seat 42 to allow passage of coolant past the valve and into the coolant circuit inlet 31.

The union between the manifold outlet port 21 and the supply coupling 29 is shown in FIG. 2B. The supply coupling 29 engages with the port 21 and may be sealed by an O-ring 47 which may engage with an annular groove on the supply coupling (not shown) or may seal on the face 53 of the supply coupling 29. The projections 30 on the distal end 50 of the supply coupling 29 pass through one or more flow passages 46 upon connection, to push the valve diaphragm 43 off its seat 42 allowing passage of the coolant. This approach is illustrated in more detail in FIG. 2F.

FIG. 2C illustrates a supply coupling 29, having a distal end 50. In one approach, the distal end may comprise projections 30 configured to cause the manifold outlet valve 23 to open upon connection of the coupling to the outlet port. This allows cooling fluid to enter the device coolant fluid supply line 11 via the coolant circuit coolant inlet 31. The supply coupling may have a generally frustoconical portion 53 distally, configured to engage the manifold outlet port 21, and may have an annular groove 51 to engage an O-ring 47 of the outlet port 21.

Figure 3A:
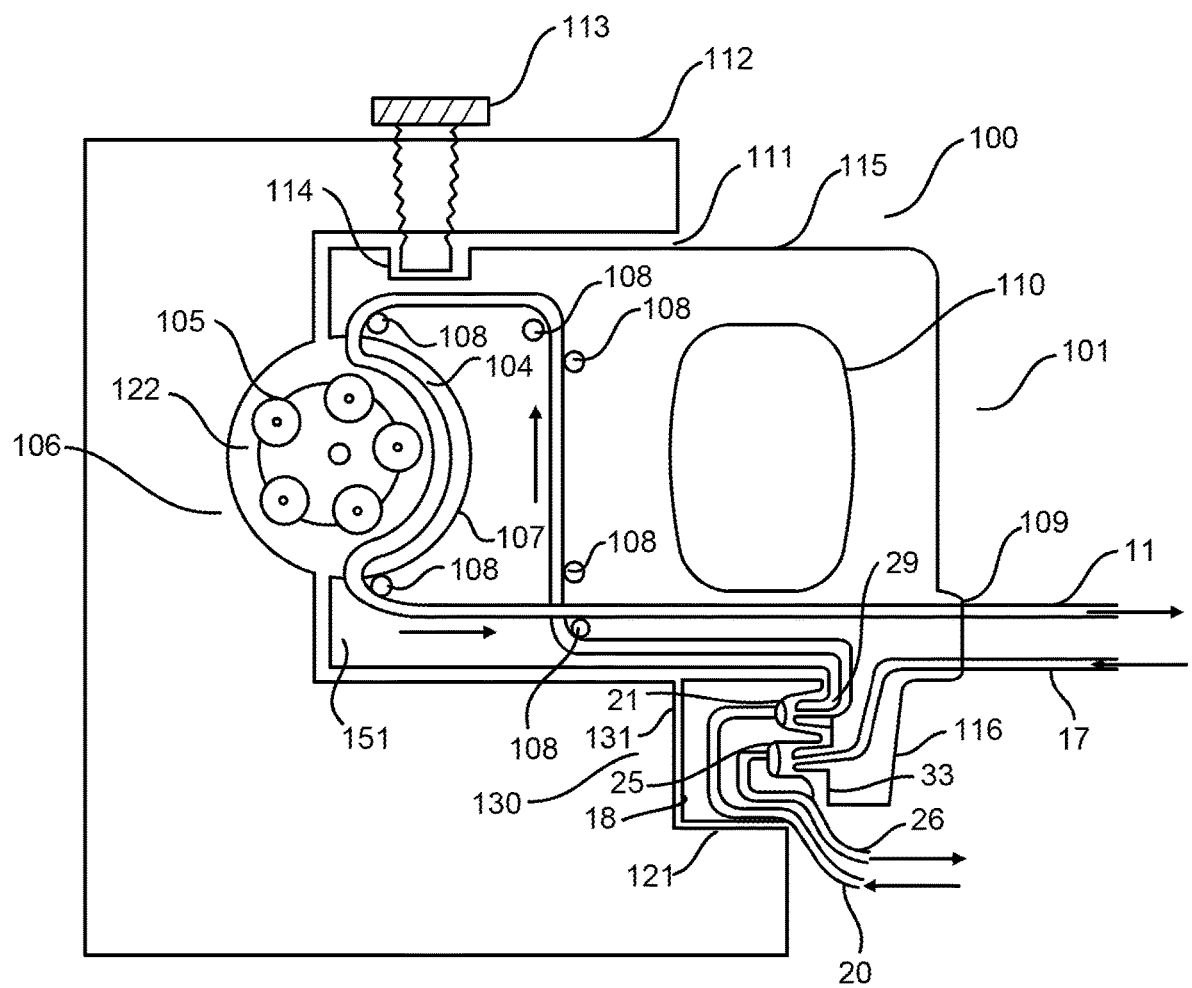
FIGS. 3A-B illustrate a cartridge as further described herein, operating with a peristaltic pump.
Figure 3B:
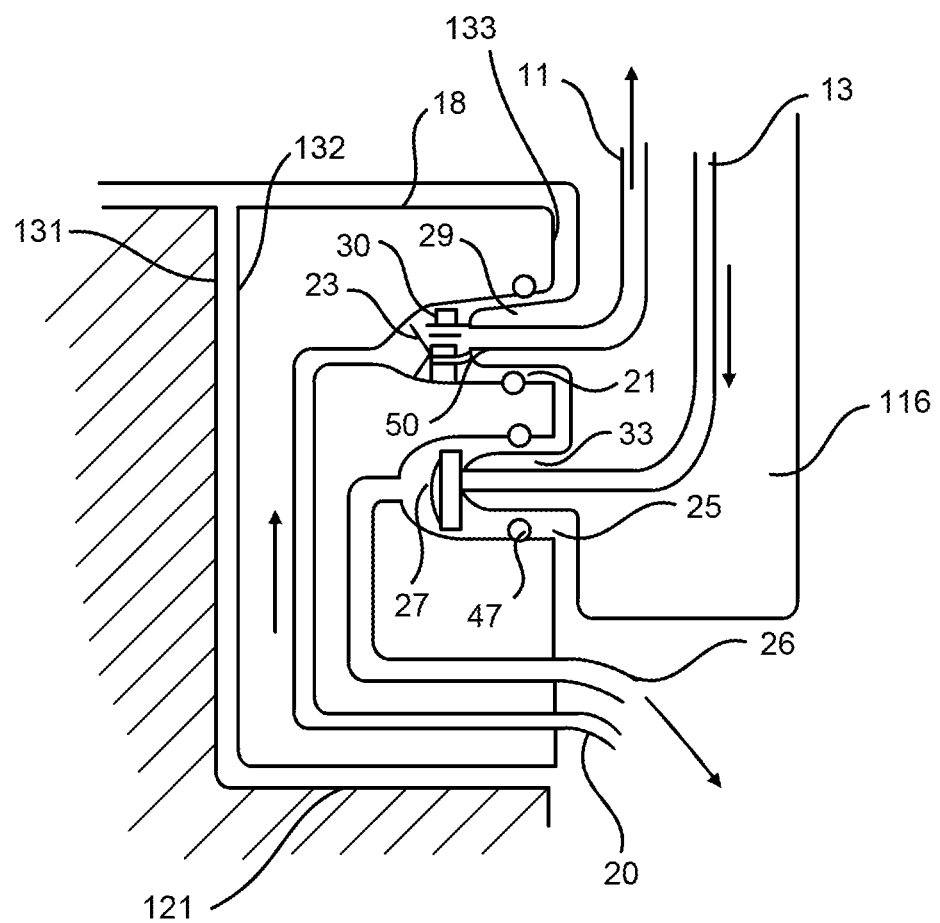

FIGS. 3A-B illustrate simplified representations of a cartridge, pump and manifold arrangement.

A portion of the cooling system for a surgical ablation device 100 is shown in FIG. 3a. A cartridge 101 is configured to hold a pump tube 104, against the rollers 105 of a peristaltic pump 106. The pump tube 104 may be (as illustrated) an integral part of the device coolant supply line 102, although in other arrangements, the pump tube may be a separate tube fluidly connected to the supply or return line. The ablation device 100 is not shown in this illustration. In operation the rotating pump rollers 105, may act upon the pump tube 104 to drive the cooling fluid towards the surgical ablation device 100. The pump tube 104 may be compressed against the surface 107 to assist the peristaltic action of the pump 106. The device coolant supply line 11 may be guided around the cartridge by a series of pegs 108 and terminates in a supply coupling 29. A device coolant return line 17 may enter the cartridge at opening 109. It may terminate at a return coupling 33. The cartridge may be equipped with a grip 110, so that it can be grasped and pressed forward into an opening 111 of the peristaltic pump housing 112 which enables the pump tube 104 to be urged against the rollers 105 of the peristaltic pump 106. The cartridge may then be held in place by a clamping mechanism, which in this case is a clamping screw 113, which acts against an indentation 114 in the cartridge housing 115.

Both the supply coupling 29 and the return coupling 33 may be mounted on an extension of the cartridge 116. FIGS. 3A-B illustrate an example of a manifold support 130 which may have a shelf 121 and a receiving surface 131; the support may receive the manifold 18. Shelf 121 may provide a support for the manifold 18, whist the system is assembled. The manifold support 130 can hold the manifold 18 in spatial arrangement with the peristaltic pump head 122, such that connection of the supply coupling 29 and the return coupling 33 with the manifold fluid outlet port 21 and the manifold fluid inlet port 25 respectively, may also bring the pump tube 104 into functional engagement with the pump head 122. Clamping the cartridge, can also hold the manifold in engagement with the manifold support 130. This may then assist in holding the arrangement in place.

The manifold 18 has a coolant system supply line 20 in fluid communication with a fluid source (see 19 on FIG. 1) which may, for example be an IV bag. The supply line 20 delivers cooling fluid to the manifold 18, shown here simplified for ease of illustration. Cooling fluid is delivered to the manifold fluid outlet port 21. The port may have a valve, 23 which may be opened upon connection of the supply coupling 29. In one approach, this may be achieved by projections 30 on the distal end 50 of the supply coupling 29, so that the coolant can flow into the device coolant supply line 11.

Similarly a manifold fluid inlet port 25 may also comprise a valve 27. This can be opened in the same manner as outlet valve 23, but the valve 27, may also be opened by the fluid pressure of the fluid return from the device 100 via the device coolant return line 17. The cooling fluid may then pass, via the manifold 18, into the coolant system return line 26 and thence to waste or to be recycled.

FIG. 3B illustrates a detailed view of the arrangement of the manifold 18, the shelf 121 and the cartridge extension 116. The manifold 18 is shown here in a simplified view with only one manifold inlet port 25 and outlet port 21. The manifold 18 has a rear face 132 and a front face 133. Bringing the pump tube 104 into functional engagement with the pump rollers 105, may advantageously connect the supply coupling 29, to the manifold fluid outlet port 21 and open the manifold outlet valve 23. It may also connects the return coupling to the manifold inlet port 25 and in one approach, trap the manifold 18 between the support surface 131 and the cartridge projection 116. The rear face 132 of the manifold 18 may then be held against the support surface 131.

Figure 4:
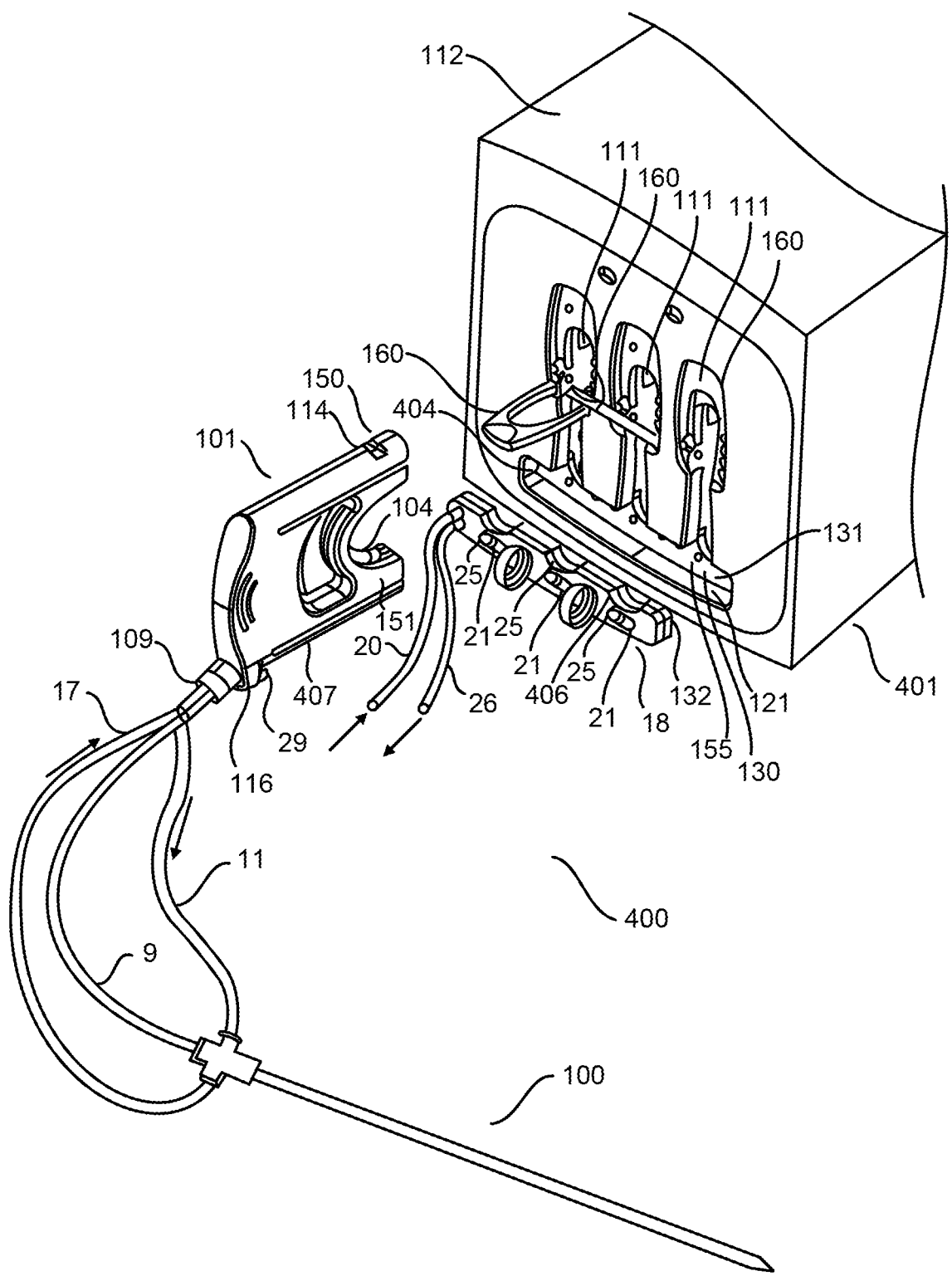
FIG. 4 illustrates a surgical ablation system having a cooling system as further described herein.

FIG. 4 is a schematic diagram of a cooling system 400, showing a pump control box 401, having a pump housing 450 incorporating a peristaltic pump arrangement having three sets of pump head rollers (not visible in this view) and suitable for controlling the cooling of three separate ablation devices, one of which is illustrated 403. Refer also to FIGS. 3A and 3B.

A manifold 18 is connected to a cooling system supply line 20 which distributes cooling fluid to the manifold fluid outlet port 21 from a cooling fluid source (not shown) and a cooling system return line 26 receiving returning cooling fluid from the manifold fluid inlet port 25 and returning it to the source or to waste. The manifold 18 is received by a manifold support 130, which may be configured to hold the manifold in place during assembly of the system and which, in this case, is in the form of a recess 404 in the control box 401 shaped to receive the manifold 18. The recess has a shelf 121, and a receiving surface 131.

With reference to FIG. 3A as well as FIG. 4, the pump housing 112 may have a recess 111 configured to receive the distal end 150 of the cartridge 101. The peristaltic pump rollers 105 may be positioned within the recess 111 (FIG. 3A). The cartridge 101 is configured to present the pump tube 104 to the pump head rollers (105, FIG. 3A), such that the pump tube 104 is brought into functional engagement with the rollers 105. The manifold 18 may comprise a guide which may be, for example in the form of a recess 406. The guide 406 may be configured to engage the cartridge 101 and to guide it into the recess 405. For example, the guide 406 may be configured as a channel having a curved section which may be configured to engage a curved under-surface 407 of the cartridge 101.

The ablation device 100 in this case is in the form of a needle and may be for example a microwave ablation needle or an Rf ablation needle. The device may have a cable bundle 9, which comprises an energy delivery cable for delivering the ablation energy to the device from an energy supply (not shown see FIG. 1) and may additionally comprise cables from sensors such as temperature sensors 28 and/or flow sensors 38 within the device, to a control system. The cables may terminate at one or more connectors (not shown in this view, but which may be disposed at the distal end 150 of the lower arm 151 of the cartridge, for example) for connecting the cables to the energy supply and control system and/or data acquisition system, so that the connections are made when the pump tube 104 is engaged with the pump rollers 105.

The device 100 has a device cooling circuit that comprises a device coolant supply line 11 and a device coolant return line 17, in fluid communication with each other via one or more device coolant passageways 14, 15, 16 (not shown in this diagram, see FIG. 1 for examples). The device coolant supply line can pass into the cartridge 101 at the opening 109 and terminates at the supply coupling 29. The supply coupling may be disposed on a cartridge extension 116. A portion of the device coolant supply line 11 may be configured as the pump tubing 104 for a peristaltic pump, such that operation of the pump can drive coolant fluid to circulate through the device coolant passages 14, 15, 16. The device coolant return line 17 terminates at the return coupling 33, which can be situated adjacent to the supply coupling (see FIG. 4).

In operation, the cooling system supply line 20 may be connected to the cooling system supply, for example an IV bag, via a standard bag spike (60 FIG. 1). The cooling system return line 26 may likewise be connected to waste or may also be connected to the IV bag. This allows cooling fluid to enter the manifold 18, but, since the inlet valves 27 and outlet valves 23 are normally closed the manifold 18 does not leak. The manifold 18 may be received in a manifold support 130. The manifold 18 may be configured for releasable engagement with the pump housing 112. To this end, the manifold may comprise one or more releasable couplings configured to engage with the pump housing 112, for example a coupling may extend from the rear face 132, of the manifold 18 and engage with a coupling on the pump housing 112. In one approach, pegs extending from the rear of the manifold 18 and not visible in this view, engage with a series of peg receivers 155 on the housing, for example on the support face 130 of the manifold support 130 to provide a releasable coupling between the manifold 18 and the pump housing 112.

The cartridge may then be pushed into the recess 111 so as to place the pump tubing 104 into functional engagement with the pump rollers 105. The cartridge may be guided into place by sliding engagement of the curved under-surface 407 of the cartridge 101 with the guide recess 406 on the manifold 18 which provides an appropriate alignment to both connect the pump tube 104 to the rollers 105, and also to connect the supply coupling 29 to the manifold outlet port 21 and the return coupling 33 to the manifold inlet port 25. Connecting the supply coupling 29 to the manifold outlet port 21 may then open the manifold outlet valve 23 and place the cooling system supply line 20 in fluid communication with the device coolant supply line 11, completing the supply of coolant to the device. Operation of the pump rollers may then then prime the cooling system.

Once in place the cartridge may be held in place by operation of a clamp arm 160, which operates a clamping mechanism (not shown) to engage the cartridge 101 and hold it in place.

Further devices may be added to the system, for example, in FIG. 4, up to two additional ablation devices may be added to the system, simply by plugging their cartridges 101 directly into the recess 111 to engage the pump tube 104 with the pump rollers 105 of the peristaltic pump head and operating the clamp 160 to hold the cartridge in place.

Figure 5A:
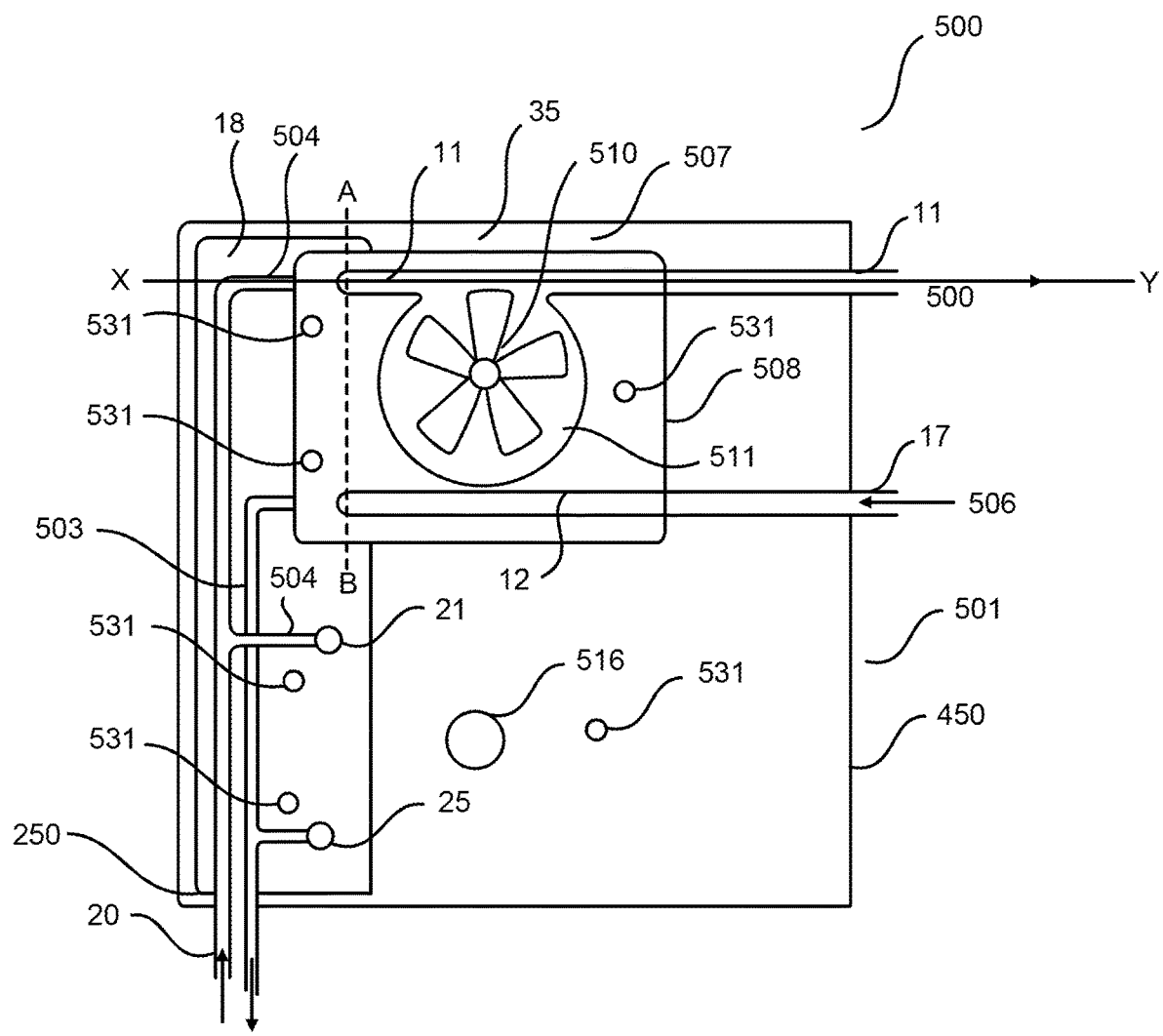
FIGS. 5A-B illustrate an embodiment of a surgical ablation device cooling system having a pumping portion comprising a demountable pump head.
Figure 5B:
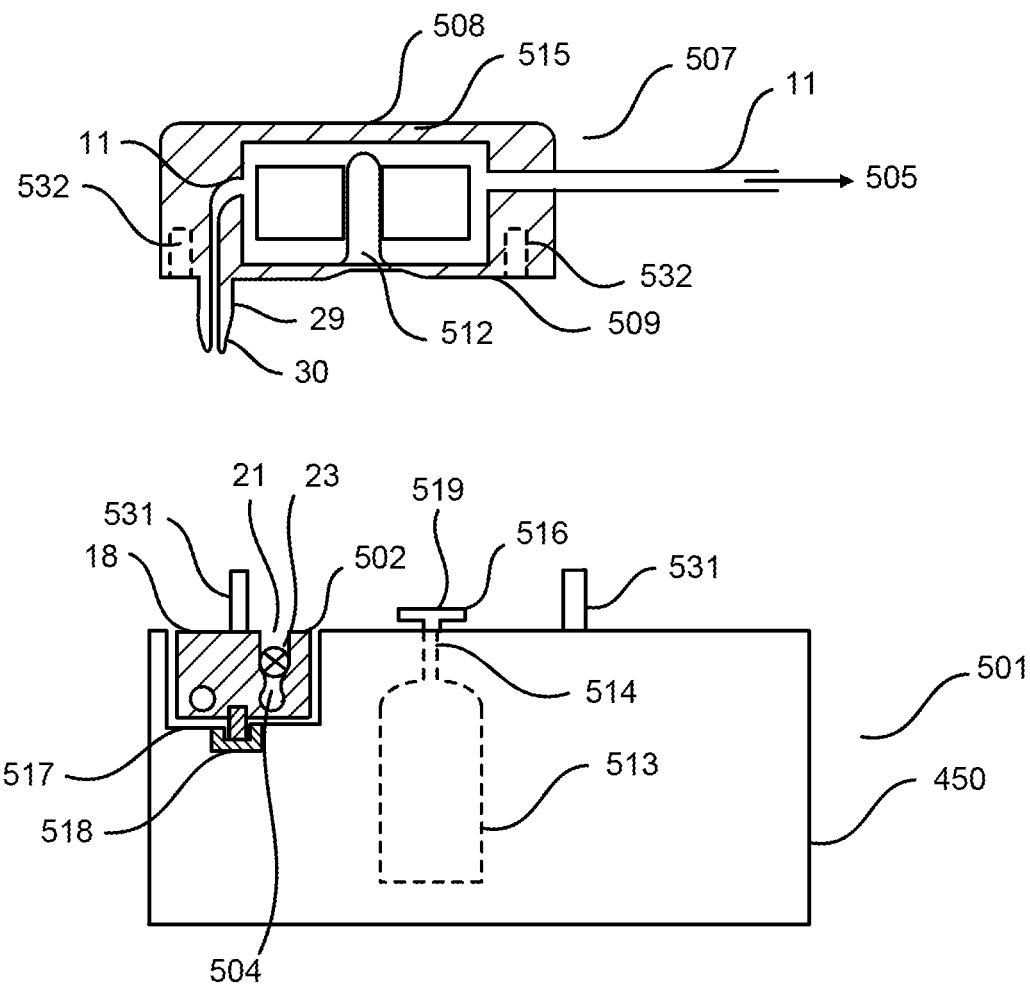
Figure 5C:
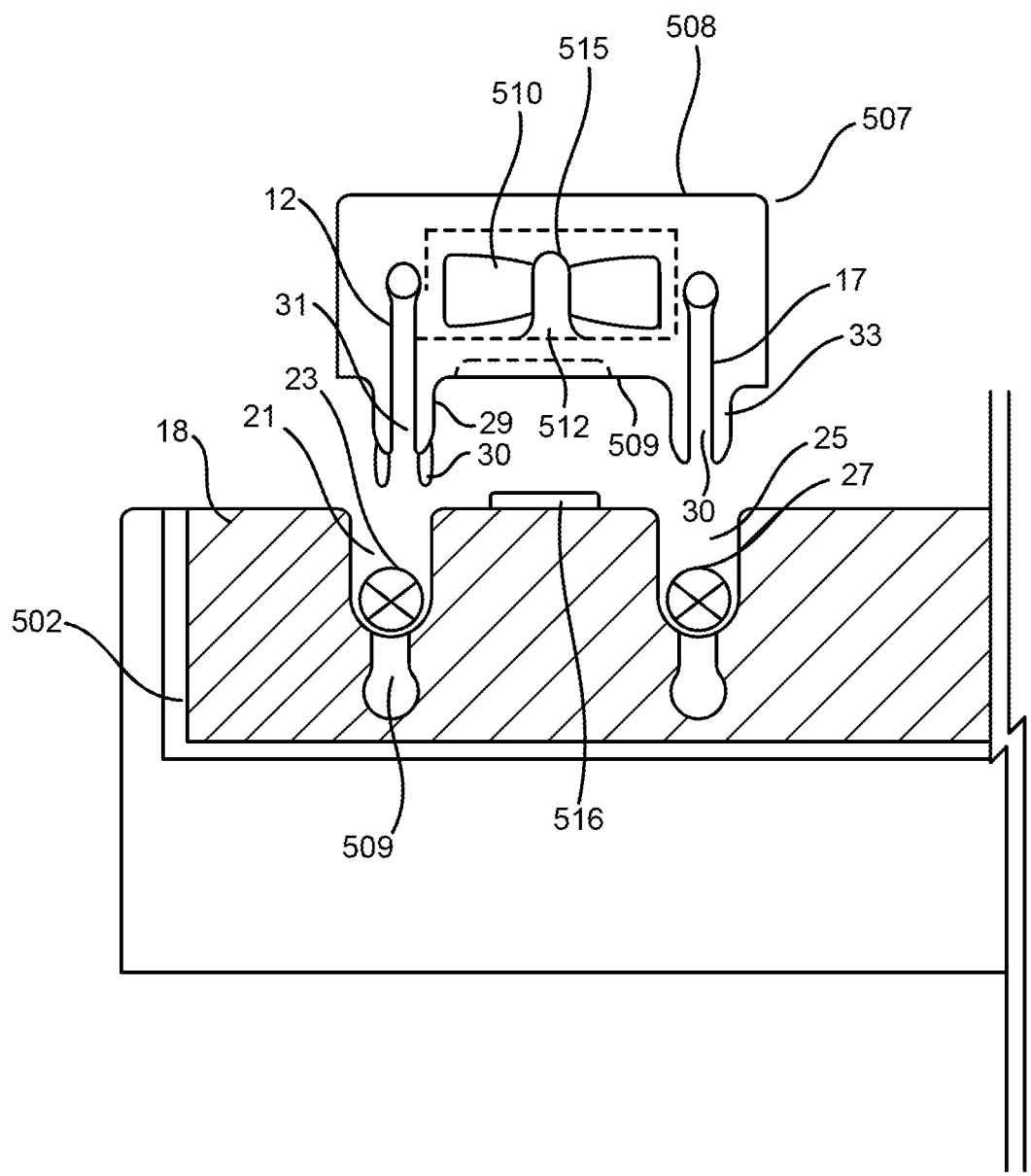
FIG. 5C shows a partial sectional side view at A-B.

FIGS. 5A-C illustrate an embodiment of a surgical ablation device cooling system having a pumping portion comprising a demountable pump head. FIG. 5A shows a plan view of a cooling system 500 having a pump 501 manifold 18 and a cartridge 508 comprising a demountable pump head 507, whilst FIG. 5B shows a sectional side view at X-Y. FIG. 5C shows a partial sectional side view at A-B.

FIG. 5A shows a plan view of a cooling system 500. The cooling system is configured to cool two ablation devices 2. The cooling system comprises one pump 501 comprising two pump drives 519, in this case driven by two motors 513. The system comprises a single manifold 18, configured to connect two devices 2 to the cooling fluid supply 19. Only one pump head 507 is present for ease of illustration.

The pump 501 has a pump housing 450. The pump housing may have a recess 502 for receiving a cooling fluid distribution manifold 18. In the illustration the manifold 18 receives coolant fluid from a coolant fluid source 19 (see e.g. FIG. 1), via a coolant system supply line 20. The coolant system supply line 20 may be permanently connected to the manifold 18 at the manifold fluid supply inlet 250 although in some embodiments, it may be demountable and connectable via a connector. The coolant fluid passes down a manifold inlet conduit 503 and is supplied via inlet conduit branches 504 to the manifold outlet ports 21. In some embodiments, as illustrated here, fluid supply to the manifold outlet port 21 may be via a manifold outlet valve 23. The valve is normally closed to flow out of the port in the direction of the device cooling passageways (not shown) as indicated by flow arrow 505. The valve 23 may be situated at the base of the port 21.

The system also comprises a device coolant supply line 11 supplying coolant fluid to the device cooling passageways 14, 15, 16 (with reference to FIG. 1) and a device coolant return line 17 receiving cooling fluid from the device coolant passageways 14, 15, 16.

The system may comprise a pumping portion 35 which in the illustrated case, is in the form of a demountable pump head 507. The pump head 507 may be provided as a component of a cartridge 508. The cartridge may also comprise the supply coupling 29 and in some embodiments also the return coupling 33, disposed on the underside 509 of the cartridge 508. The cartridge may also comprise extensions of the device supply line 11 and the return line 17 which fluidly connect the cooling circuit inlet 31 and cooling circuit outlet 34 to the device coolant passages 14, 15, 16.

The demountable pump head may operate on any pumping principle to pump cooling fluid through the cooling circuit, but in the illustrated case, comprises a pump rotor 510 disposed with a pumping space 511, within which the pump rotor 510 acts upon the cooling fluid to pump it through the coolant circuit 34. The pump 501 may comprise a pump motor 513 and a pump drive 519 configured to drive the pump rotor. The pump motor has a pump motor spindle 514. The spindle in this case is configured for demountable connection to the pump head via the pump drive 519. In the illustrated case, the pump drive comprises a magnetic coupler 516 configured to engage with a magnetic coupler 512 in the shaft 515 of the pump rotor, in order to drive the rotor, although other coupling approaches may be used.

In some embodiments, it is advantageous that the system is configured to hold the manifold ports 21, 25 in a fixed spatial arrangement with the pump 501, (particularly with the pump drive 519). Thus, in use, the manifold 18 may, for example, be placed in a recess 502. This holds the manifold in position during assembly, but also presents the ports 21, 25 in the correct arrangement for connecting to the couplings 23, 29 disposed on the cartridge 508. Holding the manifold 18 in place relative to the pump (particularly the pump drive 519 or coupling 516, has the additional advantage that it is possible to connect the couplings 29, 33 to the ports 21, 25 at the same time as connecting the pump drive 519 to the pump head 507. This is particularly useful when the pump head 507 and couplings 23, 29 are disposed on a cartridge 508, since this presents the three components in a fixed spatial arrangement suitable for engaging the ports and couplings at the same time as the pump drive and it enables all three components to be manipulated as a single piece.

The pump head can be guided into place on the drive, and the couplings into place in the ports, by guide pins 531, which engage with holes 532.

Once the manifold 18 is in place, it is possible to allow cooling fluid 530 into the manifold 18. The manifold outlet valve is closed, preventing leakage.

The cartridge 508 may be attached, to bring the pump drive 519 into engagement with the pump head 507; at the same time, the supply coupling 29 is brought into connection with the manifold outlet port 21 and the return coupling 33 is brought into engagement with the manifold inlet port 25. In the illustrated example, as the supply coupling 29 is brought into engagement with the outlet port 21, the projections 30 on the supply coupling 29 engage the manifold outlet valve 23 to cause the valve to open. This allows cooling fluid to enter the pump and to flow towards the ablation device 2. Returning fluid 506 passes through the return coupling 33 into the manifold 18. In some embodiments, such as the case illustrated in FIGS. 5A-C, a manifold inlet valve 27 controls the flow through the inlet port. In this case the valve may be a non-return valve that remains closed unless the fluid pressure is higher on the upstream (device) side. Thus returning fluid causes the manifold inlet valve 27 to open and allows the cooling fluid pass through the manifold 18 to the cooling system return line 26. From there the fluid is either passed to waste, or is recycled to the cooling fluid circuit.

We claim:

1. A surgical ablation system comprising:
   a surgical ablation device comprising a device coolant passageway for cooling at least a portion of the surgical ablation device, the passageway fluidly coupled between a device inlet and a device outlet;
   a device coolant supply line;
   a device coolant return line;
   a manifold including:
     a first manifold passageway,
     a second manifold passageway configured to be in fluid communication with a coolant system return line,
     an outlet port with a first normally-closed valve and fluidly coupled to the first manifold passageway,
     an inlet port with a second normally-closed valve and fluidly coupled to the second manifold passageway; and
   a cartridge fluidly coupled between (1) the device coolant supply line and the outlet port and (2) the device coolant return line and the inlet port, the cartridge including a cartridge input shaped to couple to the outlet port and a cartridge output shaped to couple to the inlet port,
   wherein, when the cartridge is coupled to the manifold, (1) the first normally-closed valve is opened by the cartridge to allow cooling fluid to pass into the device inlet and (2) the cooling fluid flowing from the device outlet causes the second normally-closed valve to open to allow for the cooling fluid to pass through the second manifold passageway to the coolant system return line, and
   wherein each of the surgical ablation device, the device coolant supply line, the device coolant return line, and the manifold are configured to form a closed circuit that is retained when the cartridge is coupled to the manifold to thereby open the first normally-closed outlet valve.

2. The surgical ablation system of claim 1, wherein the cartridge input and the cartridge output are disposed in an arrangement configured for simultaneous connection to the outlet port and the inlet port respectively.

3. The surgical ablation system of claim 1, further comprising a pump configured to pump the cooling fluid through the device coolant passageway.

4. The surgical ablation system of claim 3, wherein the manifold is configured for releasable engagement with the pump.

5. The surgical ablation system of claim 3, wherein the pump comprises a pump drive configured to drive a pump head to pump the cooling fluid.

6. The surgical ablation system of claim 5, further comprising a pump tube configured for releasable engagement with the pump head.

7. The surgical ablation system of claim 6, wherein the pump tube, is disposed in the cartridge to hold the pump tube in engagement with pump head rollers.

8. A system comprising:
   a surgical ablation device including a passageway for passing cooling fluid through at least a portion of the surgical ablation device, the passageway including a device inlet and a device outlet;
   a manifold including an outlet port with a first normally-closed valve and fluidly coupled to a first manifold passageway, and an inlet port with a second normally-closed valve and fluidly coupled to a second manifold passageway;
   a cartridge including a supply coupling for connection to the outlet port and a return coupling for connection to the inlet port;
   a device coolant supply line fluidly coupled between the supply coupling and the device inlet;
   a device coolant return line fluidly coupled between the return coupling and the device outlet;
   a pumping portion fluidly coupled to the device coolant supply line to pump the cooling fluid towards the surgical ablation device;
   wherein, when the cartridge is coupled to the manifold, (1) the first normally-closed valve is opened by the cartridge to allow the cooling fluid to pass into the device coolant supply line and (2) the cooling fluid flowing from the device coolant return line causes the second normally-closed valve to open and to allow the cooling fluid to pass through the second manifold passageway to a coolant system return line,
   wherein the supply and return couplings are disposed on the cartridge in an arrangement configured for simultaneous connection to the outlet port and the inlet port respectively such that the surgical ablation device is added to a closed-looped system that includes the device coolant supply line, the device coolant return line, and the manifold so as to allow the manifold to be filled with coolant prior to coupling the cartridge to the manifold and to retain the closed loop system when the cartridge is coupled to the manifold.

9. The system of claim 8, wherein the pumping portion comprises a demountable pump-head configured for releasable engagement with a pump drive.

10. The system of claim 8, wherein the pumping portion comprises a pump tube configured for releasable engagement with a pump head of a peristaltic pump.

11. The system of claim 8, wherein the pumping portion comprises a tube of a peristaltic pump and wherein the tube is disposed in cartridge.

12. The system of claim 8, wherein the simultaneous connection of the cartridge to the outlet port and the inlet port is facilitated via an opening that is formed in the manifold and in communication with the outlet port and the inlet port, the opening designed to receive the cartridge, wherein when the cartridge is fully engaged in the opening, the first normally-closed outlet valve is opened.

\* \* \* \* \*